US00PP24191P2

(12) United States Plant Patent
Luo

(10) Patent No.: US PP24,191 P2
(45) Date of Patent: Jan. 21, 2014

(54) ***KNIPHOFIA* PLANT NAMED 'KNI609'**

(50) Latin Name: *Kniphofia uvaria*
Varietal Denomination: KNI609

(75) Inventor: Shuming Luo, Dulwich Hill (AU)

(73) Assignee: Amerinova Properties LLC, Bonsall, CA (US)

( * ) Notice: Subject to any disclaimer, the term of this patent is extended or adjusted under 35 U.S.C. 154(b) by 73 days.

(21) Appl. No.: 13/506,274

(22) Filed: Apr. 7, 2012

(51) Int. Cl.
*A01H 5/00* (2006.01)

(52) U.S. Cl.
USPC ..... Plt./443

(58) Field of Classification Search
USPC ..... Plt./443
See application file for complete search history.

*Primary Examiner* — Annette Para
(74) *Attorney, Agent, or Firm* — C. A. Whealy

(57) ABSTRACT

A new and distinct cultivar of *Kniphofia* plant named 'KNI609', characterized by its upright plant habit; moderately vigorous growth habit; freely flowering habit; repeat flowering over a long period of time; and pale yellow-colored flowers.

2 Drawing Sheets

Botanical designation: *Kniphofia uvaria.*
Cultivar denomination: 'KNI609'.

BACKGROUND OF THE INVENTION

The present invention relates to a new and distinct cultivar of *Kniphofia* plant, botanically known as *Kniphofia uvaria* and hereinafter referred to by the name 'KNI609'.

The new *Kniphofia* originated from a cross-pollination conducted by the Inventor in 1996 of two unnamed proprietary selections of *Kniphofia uvaria*, not patented. The new *Kniphofia* was discovered and selected by the Inventor as a single flowering plant from within the progeny of the stated cross-pollination grown in a controlled greenhouse environment in Cobbitty, New South Wales, Australia in November, 2006.

Asexual reproduction of the new *Kniphofia* plant by vegetative divisions in a controlled environment in Macquarie Fields, New South Wales, Australia since December, 2006 has shown that the unique features of this new *Kniphofia* plant are stable and reproduced true to type in successive generations.

SUMMARY OF THE INVENTION

Plants of the new *Kniphofia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'KNI609'. These characteristics in combination distinguish 'KNI609' as a new and distinct *Kniphofia* plant:

1. Upright plant habit.
2. Moderately vigorous growth habit.
3. Freely flowering habit.
4. Repeat flowering over a long period of time.
5. Pale yellow-colored flowers.

Plants of the new *Kniphofia* can be compared to plants of the female parent selection. Plants of the new *Kniphofia* differ from plants of the female parent selection in the following characteristics:

1. Plants of the new *Kniphofia* are shorter than plants of the female parent selection.
2. Plants of the new *Kniphofia* and the female parent selection differ in flower color as plants of the female parent selection have lighter yellow-colored flowers.

Plants of the new *Kniphofia* can be compared to plants of the male parent selection. Plants of the new *Kniphofia* differ from plants of the male parent selection in the following characteristics:

1. Plants of the new *Kniphofia* and the male parent selection differ in leaf color.
2. Plants of the new *Kniphofia* repeat flower whereas plants of the male parent selection do not repeat flower.
3. Plants of the new *Kniphofia* and the male parent selection differ in flower color as plants of the male parent selection have orange-colored flowers.

Plants of the new *Kniphofia* can also be compared to plants of *Kniphofia uvaria* 'Little Maid', not patented. In side-by-side comparisons conducted in Macquarie Fields, New South Wales, Australia, plants of the new *Kniphofia* differed from plants of 'Little Maid' in the following characteristics:

1. Plants of the new *Kniphofia* flowered earlier than plants of 'Little Maid'.
2. Plants of the new *Kniphofia* and 'Little Maid' differed in flower color as plants of 'Little Maid' had lighter yellow-colored flowers.

BRIEF DESCRIPTION OF THE PHOTOGRAPHS

The accompanying colored photographs illustrate the overall appearance of the new *Kniphofia* plant showing the colors as true as it is reasonably possible to obtain in colored reproductions of this type. Colors in the photographs may differ slightly from the color values cited in the detailed botanical description which accurately describe the colors of the new *Kniphofia* plant.

The photograph on the first sheet comprises a side perspective view of a typical plant of 'KNI609' grown in a container.

The photograph on the second sheet is a close-up view of a typical inflorescence of 'KNI609'.

DETAILED BOTANICAL DESCRIPTION

The aforementioned photographs and following observations, measurements and values describe plants grown in containers during the winter in a polyethylene-covered greenhouse in Bonsall, Calif. and under cultural practices which approximate commercial production. During the production of the plants, day temperatures ranged from 21° C. to 27° C., night temperatures ranged from 16° C. to 20° C. and light levels ranged from 4,200 to 5,000 foot-candles. Plants were six months old when the photographs and description were taken. In the following description, color references are made to The Royal Horticultural Society Colour Chart, 2007 Edition, except where general terms of ordinary dictionary significance are used.

Botanical classification: *Kniphofia uvaria* 'KNI609'.

Parentage:

*Female, or seed, parent*.—Unnamed proprietary selection of *Kniphofia uvaria*, not patented.

*Male, or pollen, parent*.—Unnamed proprietary selection of *Kniphofia uvaria*, not patented.

Propagation:

*Type*.—By vegetative divisions.

*Root description*.—Thick, fleshy; white in color.

*Rooting habit*.—Moderately freely branching; medium density.

Plant description:

*Plant and growth habit*.—Herbaceous perennial; upright plant habit; basal rosette of leaves; flowering stems developing from the center of the basal rosette of leaves; moderately vigorous growth habit.

*Plant height, soil level to top of leaves*.—About 32 cm.

*Plant height, soil level to top of inflorescences*.—About 55 cm.

*Plant diameter*.—About 39 cm.

Foliage description:

*Arrangement*.—Alternate; simple; sessile; grass-like.

*Length*.—About 30.5 cm.

*Width*.—At the base, about 6 mm; mid-section, about 4 mm.

*Shape*.—Lanceolate; strongly keeled.

*Apex*.—Apiculate.

*Base*.—Truncate, clasping.

*Margin*.—Entire.

*Texture, upper and lower surfaces*.—Smooth, glabrous.

*Venation pattern*.—Parallel.

*Color*.—Developing leaves, upper and lower surfaces: Close to 144A. Fully expanded leaves, upper surface: Close to N137A; venation, close to N137A. Fully expanded leaves, lower surface: Close to N137A to N137B; venation, close to N137A to N137B.

Flower description:

*Flower arrangement and habit*.—Single funnelform flowers arranged on upright terminal racemes; freely flowering habit with about 96 flowers developing per inflorescence; flowers face outward to slightly downward.

*Fragrance*.—None detected.

*Natural flowering season*.—Long flowering period, plants flower repeatedly from spring to autumn in southern California.

*Flower longevity*.—Individual flowers last about four to seven days on the plant; flowers not persistent.

*Inflorescence height*.—About 19.5 cm.

*Inflorescence diameter*.—About 3.6 cm.

*Flower diameter*.—About 3.5 mm.

*Flower length*.—About 2 cm.

*Flower buds*.—Length: About 1.6 cm. Diameter: About 2.6 mm. Shape: Columnar. Color: Close to N144A.

*Corolla*.—Arrangement: Six segments fused into a narrow tube; apices free. Length: Total, about 2 cm; free apices, about 4 mm. Width: Total, about 3.5 mm; free apices, about 2 mm. Lobe shape: Rounded. Apex: Obtuse. Margin: Entire. Texture, upper and lower surfaces: Smooth, glabrous. Color: When opening, inner and outer surfaces: Close to 144A to 144C. Fully opened, inner and outer surfaces: Close to 4A to 4B; color does not change with development.

*Sepals*.—None observed.

*Peduncles*.—Length: About 55 cm. Diameter: About 2 mm. Strength: Strong. Aspect: Upright to slightly outwardly. Texture: Smooth, glabrous. Color: Close to 144A.

*Pedicels*.—Length: About 1 mm. Diameter: About 1 mm. Strength: Strong. Aspect: Horizontal to bending downward with development. Texture: Smooth, glabrous. Color: Close to 146A.

*Reproductive organs*.—Stamens: Quantity: About six per flower. Filament length: About 1.1 cm. Filament color: Close to NN155D. Anther shape: Oblong. Anther length: About 1 mm. Anther color: Close to 8A. Pollen amount: None observed. Pistils: Quantity: One per flower. Pistil length: About 1.5 cm. Style length: About 1.3 cm. Style color: Close to 145C. Stigma shape: Rounded. Stigma color: Close to 146A Ovary color: Close to 146D. Seeds and fruits: Seed and fruit development have not been observed on plants of the new *Kniphofia*.

Garden performance: Plants of the new *Kniphofia* have been observed to have good garden performance and to tolerate wind, rain, high temperatures of about 35° C. and to be winter hardy to USDA Hardiness Zone 7.

Pathogen & pest resistance: Plants of the new *Kniphofia* have not been observed to be resistant to pathogens and pests common to *Kniphofia*.

It is claimed:

1. A new and distinct *Kniphofia* plant named 'KNI609' as illustrated and described.

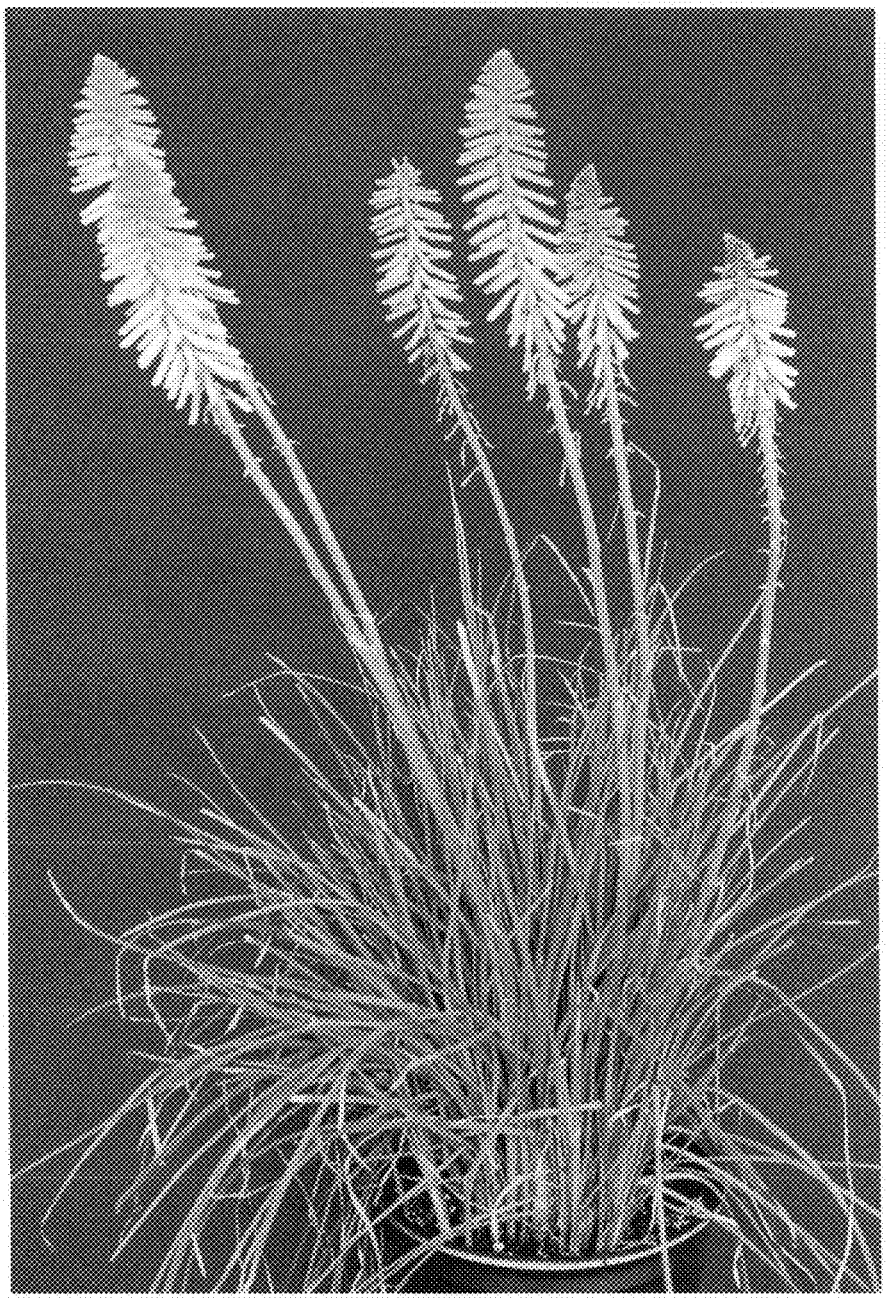

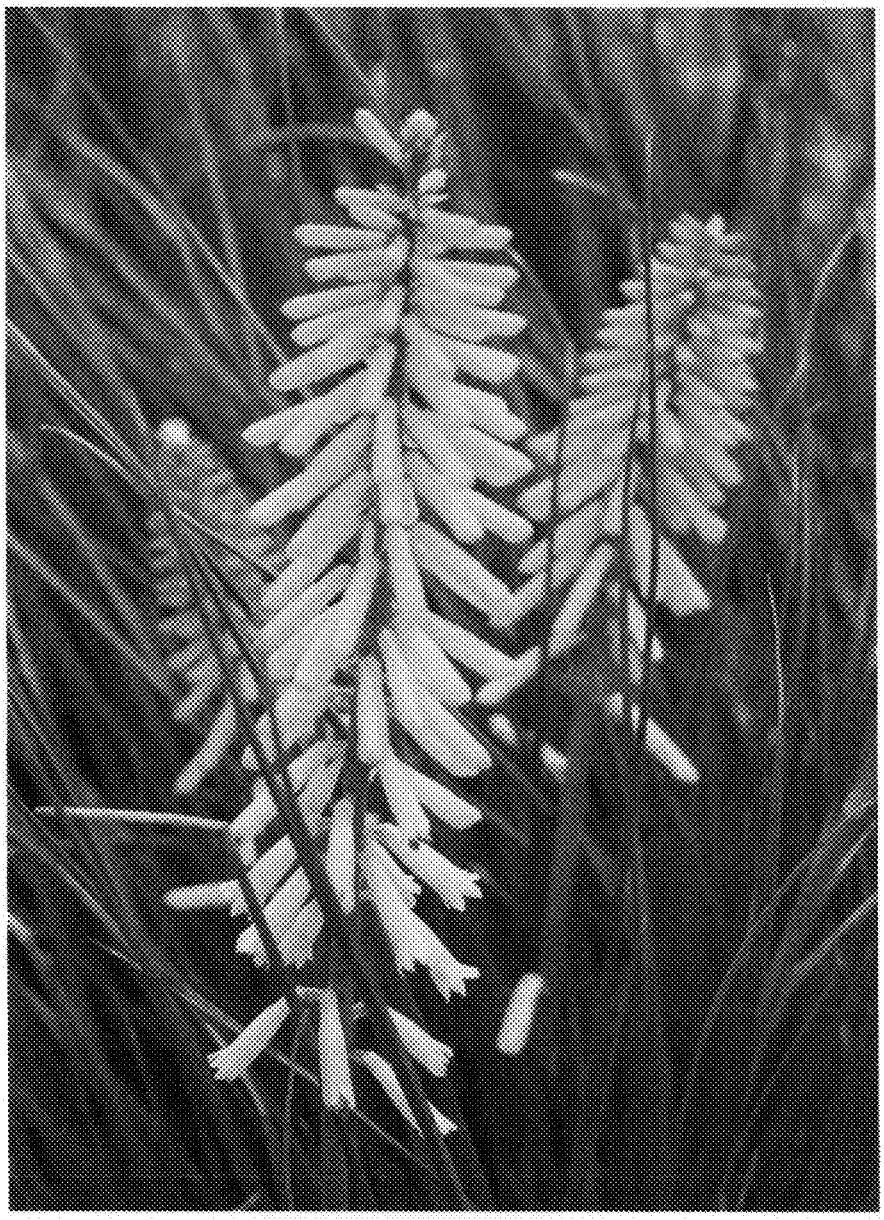

* * * * *